United States Patent
Johnson et al.

(10) Patent No.: US 9,079,012 B2
(45) Date of Patent: Jul. 14, 2015

(54) METHODS FOR SECURING ELECTRODE LEADS

(75) Inventors: Corinne H. Johnson, Seattle, WA (US); Jay Miazga, Seattle, WA (US)

(73) Assignee: ADVANCED NEUROMODULATION SYSTEMS, INC., Plano, TX (US)

( * ) Notice: Subject to any disclaimer, the term of this patent is extended or adjusted under 35 U.S.C. 154(b) by 842 days.

(21) Appl. No.: 13/354,501

(22) Filed: Jan. 20, 2012

(65) Prior Publication Data

US 2012/0110844 A1    May 10, 2012

Related U.S. Application Data

(62) Division of application No. 11/858,810, filed on Sep. 20, 2007, now Pat. No. 8,126,529.

(60) Provisional application No. 60/846,652, filed on Sep. 22, 2006.

(51) Int. Cl.
*H01R 43/00* (2006.01)
*A61N 1/04* (2006.01)
*A61N 1/05* (2006.01)

(52) U.S. Cl.
CPC .............. *A61N 1/048* (2013.01); *A61N 1/0476* (2013.01); *A61N 1/05* (2013.01); *Y10T 29/49185* (2015.01)

(58) Field of Classification Search
CPC .. H01R 4/183; H01R 4/5033; H01R 13/5224; A61N 1/048; A61N 1/0476; A61N 1/05; Y10T 29/49185

USPC ................... 29/857, 861–853, 876, 861–863; 174/84 C; 607/116, 129; 439/359, 909
See application file for complete search history.

(56) References Cited

U.S. PATENT DOCUMENTS

| | | | |
|---|---|---|---|
| 3,124,641 A | * | 3/1964 | Anderson .................. 174/84 C |
| 3,421,511 A | | 1/1969 | Wingrove et al. |
| 3,654,933 A | | 4/1972 | Hagfors |
| 4,102,331 A | | 7/1978 | Grayzel et al. |
| 4,233,987 A | | 11/1980 | Feingold |
| 4,314,095 A | | 2/1982 | Moore et al. |
| 4,332,257 A | | 6/1982 | Ayers et al. |
| 4,522,211 A | | 6/1985 | Bare et al. |
| 4,566,467 A | | 1/1986 | DeHaan |
| 4,662,382 A | | 5/1987 | Sleutz et al. |
| 4,865,566 A | | 9/1989 | Rasmussen |
| 4,903,702 A | | 2/1990 | Putz |
| 5,131,854 A | | 7/1992 | Jose et al. |
| 5,133,356 A | | 7/1992 | Bryan et al. |
| 5,197,471 A | | 3/1993 | Otero |
| 5,205,297 A | | 4/1993 | Montecalvo et al. |
| 5,215,087 A | | 6/1993 | Anderson et al. |

(Continued)

FOREIGN PATENT DOCUMENTS

GB    2045088    10/1980

*Primary Examiner* — Donghai D Nguyen

(57) ABSTRACT

Methods for securing electrode leads are disclosed. An electrode system in accordance with one embodiment includes an electrode contact, a connector attached to the electrode contact, and an electrical lead. The electrical lead can be received in an opening of the contact, with an inner surface of the opening applying a generally uniform radial pressure around a circumference of the electrical lead. For example, the contact can have a tubular shape, optionally with an elongated slit, and can be crimped around the lead to apply the generally uniform radial pressure.

8 Claims, 5 Drawing Sheets

(56) References Cited

U.S. PATENT DOCUMENTS

| | | | |
|---|---|---|---|
| 5,330,523 A * | 7/1994 | Campbell et al. | 607/129 |
| 5,445,537 A | 8/1995 | Abyzov | |
| 5,772,591 A | 6/1998 | Cram | |
| 5,846,217 A | 12/1998 | Beck et al. | |
| 6,301,493 B1 | 10/2001 | Marro et al. | |
| 6,662,035 B2 * | 12/2003 | Sochor | 607/116 |
| 6,782,293 B2 | 8/2004 | Dupelle et al. | |
| 2002/0128700 A1 | 9/2002 | Cross | |
| 2004/0093051 A1 | 5/2004 | Chinn et al. | |
| 2004/0176831 A1 | 9/2004 | Gliner et al. | |
| 2004/0243205 A1 | 12/2004 | Keravel et al. | |
| 2005/0043771 A1 | 2/2005 | Sommer et al. | |
| 2005/0085884 A1 | 4/2005 | O'Brien et al. | |
| 2008/0200925 A1 | 8/2008 | Johnson et al. | |

* cited by examiner

METHODS FOR SECURING ELECTRODE LEADS

CROSS-REFERENCE TO RELATED APPLICATION

This application is a divisional of U.S. application Ser. No. 11/858,810, filed Sep. 20, 2007, now U.S. Pat. No. 8,126,529, which claims priority to U.S. Provisional Application No. 60/846,652, filed Sep. 22, 2006, the disclosures of which are fully incorporated herein by reference.

TECHNICAL FIELD

The present invention is directed generally to methods and systems for securing electrode leads, including via a crimped tube arrangement.

BACKGROUND

Electrodes are used in a wide variety of clinical settings to provide electrical stimulation to a patient, and/or to detect electrical signals generated by the patient. In some cases, the electrodes may be implanted in the patient to provide electrical stimulation to a target neural area. For example, implanted electrodes have been used to provide electrical stimulation to the patient's brain to treat a variety of diseases and dysfunctions. In such instances, one or more electrodes are placed against or within the dura surrounding the brain, and are activated to direct electrical signals to the cortex or another portion of the brain.

One challenge associated with implanted electrodes has been to provide a flexible yet resilient connection between the electrode and the lead that supplies current to the electrode. For example, the practitioner typically wishes this connection to be flexible enough to withstand the implantation procedure and the patient's post-procedure movements, yet secure enough to maintain electrical continuity over many months or years. If the connection is not flexible enough, it may break after long periods of use. On the other hand, if the connection is not robust enough, it may also fail. Accordingly, there is a need for an electrode/lead connection that is both flexible and secure.

DETAILED DESCRIPTION

Overview

The present disclosure is directed to electrode systems with contact assemblies that secure electrode leads to contacts for applying electrical signals or fields to a patient, and/or sensing electrical signals or fields in the patient. Many embodiments of the contact assemblies are described in connection with electrode systems for use in cortical electrical stimulation. The contact assemblies and electrode systems, however, can be used in other applications.

FIGS. 1-5 illustrate several apparatus and methods of electrode systems with contact assemblies for applying or sensing electrical energy to a patient. Although specific details of the invention are set forth in the following description and these figures, one skilled in the art will understand that the present invention will have additional embodiments, and that other embodiments of the invention may be practiced without several of the specific features explained in the following description. Where the context permits, singular or plural terms may also include the plural or singular term, respectively. Moreover, unless the word "or" is expressly limited to mean only a single item exclusive from other items in reference to a list of at least two items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same features and/or types of other features and components are not precluded.

Embodiments of Electrode Systems and Contact Assemblies

Figure 1:
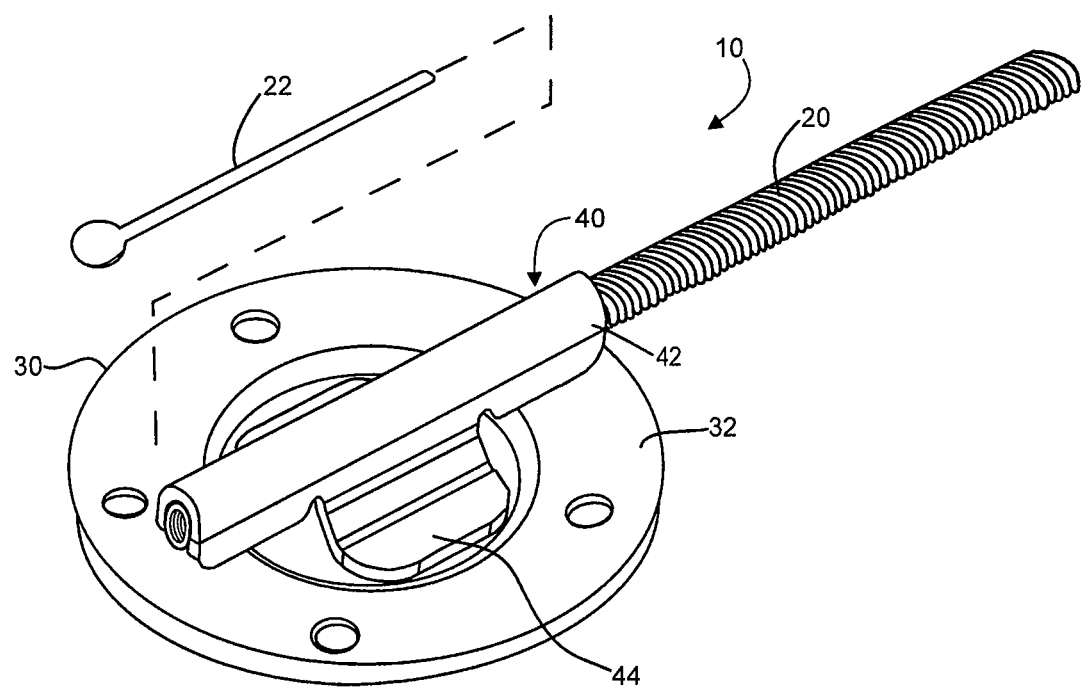
FIG. 1 is isometric view of a contact assembly of an electrode system in accordance with an embodiment of the invention.

FIG. 1 is an isometric view of one embodiment of a contact assembly 10 for use in an electrode assembly to deliver or sense electrical energy in a human or other mammalian body. In this embodiment, the electrode assembly 10 includes a lead 20 configured to transmit electrical signals, a contact 30 configured to deliver/receive electrical signals to/from the lead 20, and a connector 40 that secures the lead 20 to the contact 30. The embodiment of the connector 40 shown in FIG. 1 has a lead interface 42 configured to exert at least a substantially or generally uniform radial force around at least portion of the lead 20, and a contact interface 44 configured to be connected to the contact 30. The lead interface 42 of this embodiment of the connector 40 is configured to exert at least a substantially uniform force around at least a portion of the circumference of the lead 20 where the lead interface 42 engages the lead 20. The connector 40 can accordingly be securely fixed to the lead 20 to provide a secure, robust connection between the lead 20 and the contact 30. A mandrel 22 or other internal support can be inserted into the open end of the lead 20 to prevent the lead 20 from deforming or collapsing during assembly, surgical implantation and/or operation.

The lead 20, contact 30 and connector 40 can be made from suitably electrically conductive, bio-compatible materials, such as platinum-iridium alloys, platinum, titanium, titanium alloys, gold and other metals. In certain embodiments, portions of the lead 20, contact 30 and connector 40 can be coated with a suitable bio-compatible dielectric material. The lead 20 can also be a coil as shown in FIG. 1. As explained in more detail below, the connector assembly 10 can include contacts carried by a dielectric flexible support member.

Figure 2A:
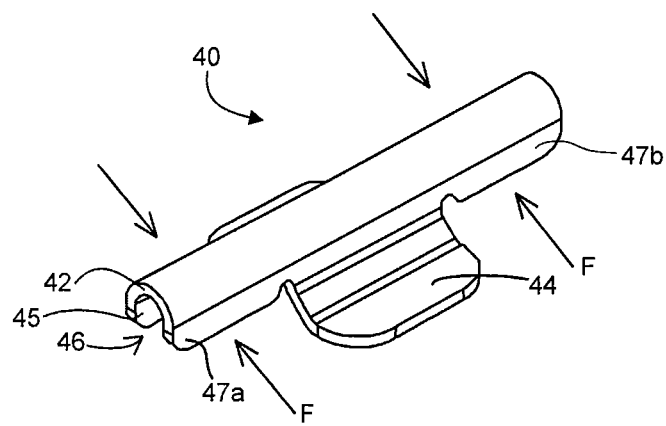
FIG. 2A is an isometric view of a connector for a contact assembly in accordance with an embodiment of the invention.

FIG. 2A is an isometric view of an embodiment of the connector 40. In this embodiment, the lead interface 42 includes an inner wall 45 configured to define a channel 46 or other opening. The channel 46 is configured to receive the lead 20. In embodiment illustrated in FIG. 2A, the channel 46 is open along the bottom such that the connector can be placed over the end of the lead 20.

In one embodiment, the inner wall 45 can have a curved portion corresponding to the cross-sectional shape of the outer surface of the lead 20. The curved portion of the inner wall 45 can have a radius that is less than an outer diameter of the lead 20 to provide a press fit with the lead. In other embodiments, however, the inner wall 45 has a diameter greater than the outer diameter of the lead 20. It is generally contemplated that an external force is applied to the lead interface 42 to crimp or otherwise press the inner wall 45 against the outer surface of the lead 20, but this may not be necessary in all embodiments. For example, forces F may be applied at a first location 47a and a second location 47b at discrete areas along the length of the lead interface 42, or forces may be applied along the entire length of the lead interface 42. The forces F that are applied to the lead interface 42 can be equal and opposite forces such that the force distribution between the lead 20 and the lead interface 42 is at least substantially uniform relative to a circumferential portion of the lead.

The connector 40 can be crimped around the electrical lead 20 using a variety of suitable techniques. For example, an automated tool can be used to perform this operation. In a particular embodiment, the tool can include specialized crimp jaws manufactured to provide the desired crimping force at the desired locations along the length of the connector. Suitable tools, including the jaws, are available from Machine Solutions, Inc. of Flagstaff, Ariz. In other embodiments, other automated techniques and tools can be used to perform this operation, and in still further embodiments, the manufacturer can use hand tools and manual techniques to perform this operation.

In other embodiments, the connector can be spread opened and then elastically return to its original configuration to press the inner wall against the lead. For example, receiving an electrical lead into the connector can include spreading opposing portions of the connector apart and inserting the lead into the opening while the opposing portions are spread apart, and the reducing a diameter of the opening by allowing the opposing portions to close on the electrical lead.

Figure 2B:
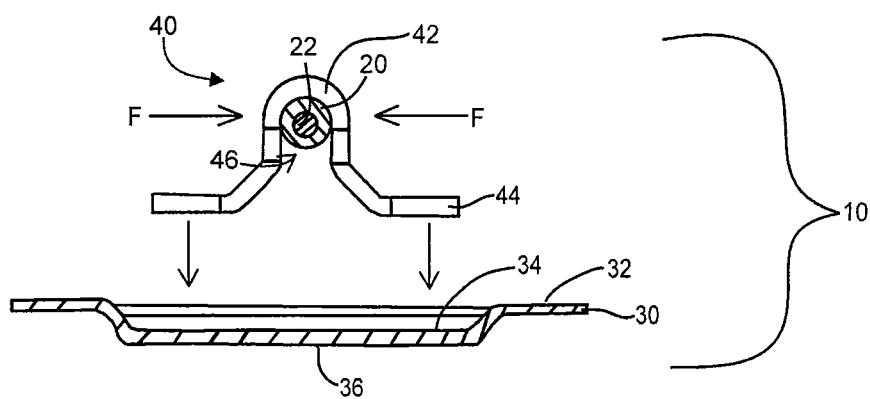
FIG. 2B is a front cross-sectional view of a partially assembled contact assembly in accordance with an embodiment of the invention.

FIG. 2B is a cross-sectional view illustrating an embodiment of the connector assembly 10 before the contact 30 has been attached to the connector 40. In this embodiment, the lead 20 is received in the channel 46 of the lead interface 42, and the connector 40 exerts at least a substantially uniform force against the lead 20. The lead 20 can further include an elongated passage in which the mandrel 22 or other type of internal support is positioned. In certain embodiments, the mandrel 22 can include a plurality of wire strands that may be wound together, and a ball (see FIG. 1) or other enlargement at the distal end of the strands to prevent the mandrel 22 from sliding proximally relative to the lead 20. The stranded arrangement can both support the lead 20 during crimping and allow the lead 20 to flex for implantation. The mandrel 22 can be made from cobalt-chromium alloys (e.g., MP35N available from Fort Wayne Metals of Fort Wayne, Ind.), titanium or titanium alloys (e.g., 35NLT, also available from Fort Wayne Metals), or other suitable materials. In operation, the mandrel 22 is inserted into the lead 20, and the lead 20/mandrel 22 assembly is inserted into the channel 46 of the lead interface 42. In other embodiments, the mandrel 22 may be a solid member. The mandrel 22, however, is optional and may not need to be included in certain embodiments. After assembly the connector 40 with the lead 20, the connector 40 can also be welded to the lead 20 to further secure the lead interface 42 to the lead 20.

The contact interface 44 is welded, adhered or otherwise attached to a backside 32 of the contact 30. In this embodiment, the backside 32 of the contact 30 can have a depression 34 in which the contact interface 44 of the connector 40 is positioned. This results in a low profile contact assembly 10. The contact 30 further includes a face 36 through which electrical energy is delivered to and/or received from the patient.

Figure 3A:
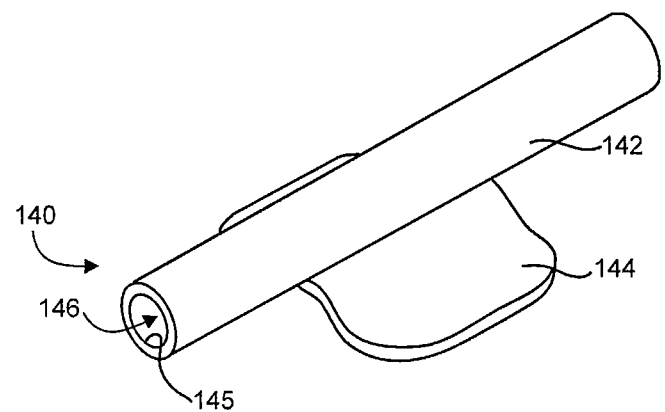
FIG. 3A is an isometric view of a connector for a contact assembly in accordance with another embodiment of the invention.

FIG. 3A is an isometric view of a connector 140 configured in accordance with another embodiment of the invention. In this embodiment, the connector 140 has a lead interface 142 having an inner wall 145 that defines an enclosed channel 146 (e.g., a lumen) and a contact interface 144. The channel 146 is configured to receive the lead 20 by sliding the lead 20 axially through the channel 146. The lead interface 42, and optionally the contact interface 144, can be made from a shape memory material (e.g., nitinol), a material having a higher coefficient of thermal expansion than the lead, or a suitable metal (platinum-iridium alloys, titanium, titanium alloys, etc.). The lead interface 42, for example, can have a first coefficient of thermal expansion and the lead 20 can have a second coefficient of thermal expansion (CTE) less than the first coefficient of thermal expansion.

Figure 3B:
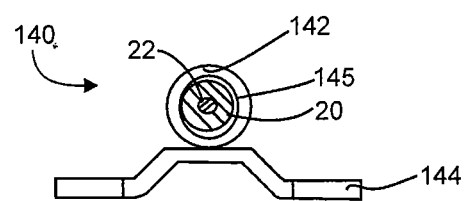
FIG. 3B is a front cross-sectional view of a partially assembled contact assembly in accordance with another embodiment of the invention.

FIG. 3B is a front cross-sectional view of a lead 20 and mandrel 22 in the channel 146 of the connector 140. In one embodiment, the lead interface 142 of the connector 140 can be crimped or otherwise forced against the outer surface of the lead as described above with respect to the connector 40. In another embodiment in which the lead interface 142 is made from a shape memory material, the lead 20 can be inserted into the channel when the lead interface 42 has a first configuration, and then the lead interface 142 can move into a second configuration suitable for implantation into a human in which the inner wall exerts a radially inward force against the lead 20. In still another embodiment in which the CTE of the lead interface 142 is greater than that of the lead 20, the connector 140 is heated to expand the channel 146 to be larger than the outer dimension of the lead, and then the lead 20 and mandrel assembly is inserted into the channel 146. The connector is then allowed to cool such that the inner wall 145 engages the outer surface of the lead 20 to exert opposing forces against the lead 20. In any of the foregoing in embodiments, the connector 140 can be optionally welded to the lead 20.

Figure 4:
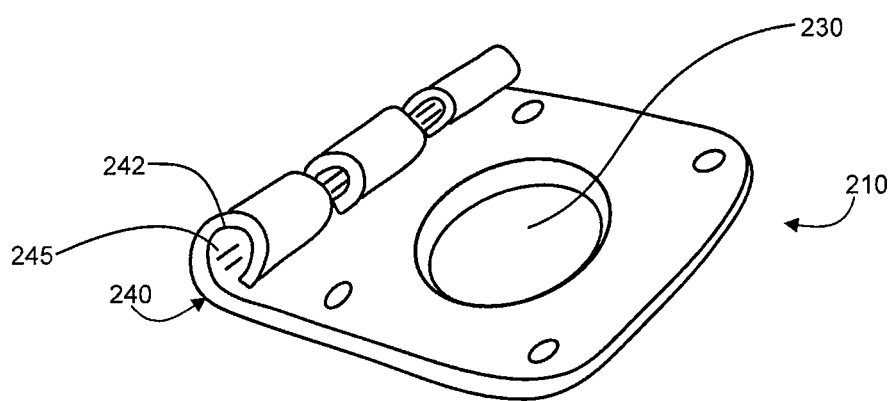
FIG. 4 illustrates a connector for a contact assembly in accordance with another embodiment of the invention.

FIG. 4 is an isometric view of a contact assembly 210 configured in accordance with another embodiment of the invention. In the illustrated embodiment, the contact assembly 210 includes a contact 230 and a connector 240 that in turn includes longitudinally spaced-apart segments 242 that collectively and/or individually define a lead interface. The segments 242 can have inner walls 245, and individual segments 242 can be crimped around a portion of the lead 20 (FIG. 1) to force the inner walls 245 against the outer surface of the lead. The lead 20 can accordingly be secured to the connector 240 using techniques generally similar to those described above. In an aspect of the embodiment shown in FIG. 4, each segment 242 is formed by rolling a corresponding tab portion of the connector 240 at least partially upon itself. Accordingly, the connector 240 and the contact 230 can be formed integrally with each other. In other embodiments, other techniques can be used to form the connector 240, and/or the connector segments 242 can be formed separately from the contact 230, and then attached to the contact 230 in a subsequent operation.

Figure 5:
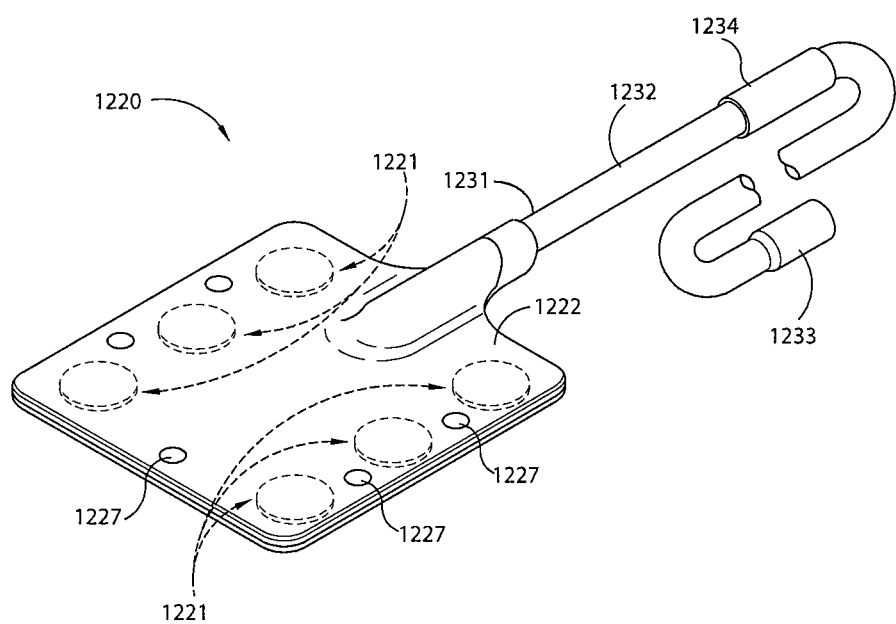
FIG. 5 is an isometric view of an electrode system in accordance with an embodiment of the invention.

In other embodiments, the system can include contacts incorporated into a signal delivery device. For example, FIG. 5 is a top, partially hidden isometric view of a signal delivery device 1220, configured to carry multiple cortical contacts 1221 in accordance with another embodiment. The contacts 1221 can be any of the embodiments of contact assemblies described above. The contacts 1221 can be carried by a flexible support member 1222 to place each contact 1221 in contact with a target neural population of the patient when the support member 1222 is implanted. Electrical signals can be transmitted to the contact 1221 via leads carried in a communication link 1231. The communication link 1231 can include a cable 1232 with one or more leads 20 (FIG. 1) that is connected to a pulse system via a connector 1233, and is protected with a protective sleeve 1234. Coupling apertures or holes 1227 can facilitate temporary attachment of the signal delivery device 1220 to the dura mater at, or at least proximate to, a target neural population. The contacts 1221 can be biased cathodally and/or anodally. In an embodiment shown in FIG. 5, the signal delivery device 1220 can include six contacts 1221 arranged in a 2×3 electrode array (i.e., two rows of three contacts each), and in other embodiments, the signal delivery device 1220 can include more or fewer contacts 1221 arranged in symmetrical or asymmetrical arrays. The particular arrangement of the contacts 121 can be selected based on the region of the patient's brain that is to be stimulated, and/or the patient's condition.

From the foregoing, it will be appreciated that specific embodiments of the invention have been described herein for purposes of illustration, but that various modifications may be made without deviating from the invention. For example, the connectors may have other arrangements that apply a generally uniform radial force to a corresponding lead, around at least a portion of the circumference of the lead. Additionally, the lead can be threadably engaged with the inner wall of any of the lead interfaces set forth above. Further, while advantages associated with certain embodiments of the invention have been described in the context of those embodiments, other embodiments may also exhibit such advantages, and not all embodiments need necessarily exhibit such advantages to fall within the scope of the invention.

We claim:

1. A method for forming an electrode connection, comprising:
   providing an electrode contact with the contact being generally planar;
   providing an electrically conductive connector with the connector having an elongated u-shaped channel, the channel having first end, second end, and middle portions, the connector further having a first tab extending from a first side of the middle portion of the channel and a second tab extending from a second side of the middle portion of the channel;
   connecting the connector to the electrode contact using the first and second tabs;
   receiving an electrical lead in the channel of the connector; and
   applying a generally uniform radial pressure around a portion of a circumference of the lead with the connector at each of the first end and second end portions of the connector.

2. The method of claim 1 wherein the step of applying radial pressure includes crimping at least one of the first end and second end portions of the connector around the electrical lead.

3. The method of claim 1, wherein the step of applying radial pressure includes crimping each of the first end and second end portions of the connector around the electrical lead.

4. The method of claim 1 wherein receiving an electrical lead includes threadably engaging the electrical lead with the connector.

5. The method of claim 1 wherein receiving an electrical lead includes spreading at least a portion of the channel apart and inserting the lead into the opening.

6. The method of claim 1 wherein receiving an electrical lead includes receiving an electrical lead that is a tightly wound about an elongated axis.

7. The method of claim 1 wherein the connector includes a shape-memory metal, and wherein applying pressure includes changing a temperature of the connector.

8. The method of claim 1 wherein the lead includes an elongated central passage, and wherein the method further comprises inserting a mandrel into the central passage before applying pressure.

\* \* \* \* \*